United States Patent
Bobic et al.

(10) Patent No.: US 6,592,588 B1
(45) Date of Patent: *Jul. 15, 2003

(54) APPARATUS FOR OSTEOCHONDRAL AUTOGRAFT TRANSPLANTATION

(75) Inventors: Vladimir Bobic, Chester (GB); Craig D. Morgan, Greenville, DE (US); Reinhold Schmieding, Naples, FL (US); Stephen S. Burkhart, San Antonio, TX (US); Philip S. O'Quinn, Naples, FL (US)

(73) Assignee: Arthrex, Inc., Naples, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/243,880

(22) Filed: Feb. 3, 1999

Related U.S. Application Data

(63) Continuation-in-part of application No. 08/885,752, filed on Jun. 30, 1997, now Pat. No. 5,919,196, which is a continuation-in-part of application No. 08/801,635, filed on Feb. 18, 1997, now Pat. No. 5,785,714, which is a continuation of application No. 08/389,492, filed on Feb. 16, 1995, now Pat. No. 5,603,716.
(60) Provisional application No. 60/024,045, filed on Aug. 16, 1996.

(51) Int. Cl.⁷ .............................................. A61B 17/32
(52) U.S. Cl. .................... 606/79; 606/167; 606/184; 600/567
(58) Field of Search ............... 606/79, 80, 86, 606/87, 88, 96, 179, 180, 167, 184, 185; 600/566, 567; 30/113.1, 113.2, 113.3

(56) References Cited

U.S. PATENT DOCUMENTS

| 493,730 A | | 3/1893 | MacKenzie ............... 606/179 |
|---|---|---|---|
| 1,585,934 A | * | 5/1926 | Muir ......................... 600/567 |
| 1,911,873 A | | 5/1933 | Balton ........................ 83/86 |
| 2,573,462 A | | 10/1951 | Lindsey ..................... 408/86 |
| 2,591,516 A | | 4/1952 | Darnell ...................... 425/280 |

(List continued on next page.)

FOREIGN PATENT DOCUMENTS

| DE | 19503504 | 3/1996 |
|---|---|---|
| HU | 214 568 B | 9/1994 |
| WO | 9106246 | 5/1991 |
| WO | WO 91/06246 | 5/1991 |

OTHER PUBLICATIONS

Laszlo Hangody, M.D., Ph.D., Gary Kish, M.D. "Mosiacplasty Osteochondral Grafting Technique Guide", Smith & Nephew Endoscopy, pp 3–10, 1996/1997.

Laszlo Hangody, M.D., Ph.D., Zoltan Karpati, "Sulyos Korulirt Terdizuleti Porckarosodas Sebeszi Kezelesenek uj Lehetosege", 1994.

(List continued on next page.)

Primary Examiner—Julian W. Woo
(74) Attorney, Agent, or Firm—Dickstein Shapiro Morin & Oshinsky, LLP

(57) ABSTRACT

Apparatus for autogenous or allograft transplantation of articular cartilage with bone from one site, such as in the knee, to another to treat chondral defects. Graft harvesters and recipient site harvesters create identically-sized donor graft osteochondral cores and recipient sockets. Collared pins disposed within the harvesters facilitate removal of the harvested cores. Windows formed in the side of the harvester tubes allow visualization of the graft, such as when being inserted into the recipient socket. A removable three-piece driver/extractor is provided to allow for impact-driving and depth control of the harvesters at the selected sites.

21 Claims, 13 Drawing Sheets

U.S. PATENT DOCUMENTS

| | | | | | |
|---|---|---|---|---|---|
| 3,512,519 | A | * | 5/1970 | Hall | 600/567 |
| 3,577,979 | A | * | 5/1971 | Van Der Gaast | 600/567 |
| 3,683,892 | A | * | 8/1972 | Harris | 600/567 |
| 3,848,601 | A | | 11/1974 | Ma et al. | 128/754 |
| 4,007,732 | A | | 2/1977 | Kvavle et al. | 128/754 |
| 4,010,737 | A | | 3/1977 | Vilaghy et al. | 606/61 |
| 4,059,115 | A | | 11/1977 | Jumashev et al. | 606/82 |
| 4,099,518 | A | * | 7/1978 | Baylis et al. | 30/113.1 |
| 4,177,797 | A | | 12/1979 | Baylis et al. | 128/754 |
| 4,596,073 | A | * | 6/1986 | Ewald | 30/113.1 |
| 4,649,918 | A | | 3/1987 | Pegg et al. | |
| 4,651,753 | A | * | 3/1987 | Lifton | 600/566 |
| 4,741,651 | A | | 5/1988 | Despres | 408/209 |
| 4,782,833 | A | | 11/1988 | Einhorn et al. | 606/80 |
| 4,790,819 | A | | 12/1988 | Li et al. | 604/59 |
| 4,820,156 | A | | 4/1989 | Ross | 433/165 |
| 4,913,143 | A | | 4/1990 | Oloff et al. | 606/170 |
| 4,936,313 | A | | 6/1990 | Burkhardt et al. | 128/751 |
| 5,092,043 | A | * | 3/1992 | Shirkey | 30/113.1 |
| 5,139,520 | A | | 8/1992 | Rosenberg | 623/13 |
| 5,152,763 | A | | 10/1992 | Johnson | |
| 5,197,967 | A | | 3/1993 | Wilson | 606/79 |
| 5,211,647 | A | | 5/1993 | Schmieding | 606/104 |
| 5,256,149 | A | | 10/1993 | Banik et al. | 604/164 |
| 5,269,786 | A | | 12/1993 | Morgan | 606/96 |
| 5,320,626 | A | | 6/1994 | Schmieding | 606/96 |
| 5,382,251 | A | | 1/1995 | Hood et al. | 606/99 |
| 5,423,823 | A | | 6/1995 | Schmieding | 606/80 |
| 5,496,326 | A | | 3/1996 | Johnson | 606/88 |
| 5,603,716 | A | | 2/1997 | Morgan et al. | 606/88 |
| 5,632,747 | A | * | 5/1997 | Scarborough et al. | 606/86 |
| 5,700,291 | A | * | 12/1997 | Kuslich et al. | 606/96 |
| 5,865,834 | A | * | 2/1999 | McGuire | 606/80 |
| 6,063,037 | A | * | 5/2000 | Mittermeier et al. | 600/567 |

OTHER PUBLICATIONS

Yoshitaka Matsusue, M.D. et al., "Arthroscopic Multiple Osetochondral Transplantation to the chondral Defect in the Knee Associated with Anterior Cruciate Ligament Disruption", The Journal of Arthroscopic and Related Surgery, 1993, pp. 318–321.

N. Gould, "Trephining Your Way," Orthopedic Clinics of North America, vol. 4, No. 1, pp. 157–164 (Jan. 1973).

V. Bobic, "Arthroscopic osteochondral autograft transplantation in anterior cruciate ligament reconstruction: a preliminary clinical study," *Knee Surg. Sports Traumatol*, Arthroscopy, vol. 3, pp. 262–264 (1996).

L. Hangody et al., "MosaicPlasty™ Osteochondral Grafting Technique Guide," Smith & Nephew Endoscopy brochure (1996).

"Acufex® MosaicPlasty™"; Smith & Nephew brochure (1997); pp. 1 and 2.

C. Fabbriciani et al., "Osteochondral Autograft in the Treatment of O.D. of the Knee," Orthopaedic Clinic, Catholic Univ., Rome, Italy (1996).

Y. Matsusue, "Arthroscopic Multiple Osteochondral Transplantation to the Chondral Defect in the Knee Associated with Anterior Crucuate Ligament Disruption," *Arthroscopy*, 9(3), pp. 318–321 (1993).

F. Yamashita, "The Transplantation of an Autogeneic Osteochondral Fragment for Osteochondrtis Dissecans of the Knee," *Clinical Orthopaedics*, No. 201, pp. 43–50 (Dec. 1985).

M. Brittberg et al., "Treatment of Deep Cartilage Defects in the Knee with Autologous Chondrocyte Transplantation," *New England J. Med.*, vol. 331, No. 14, pp. 889–895 (Oct. 6, 1994).

V. Bobic, "Arthroscopic Osteochondral Autograft Transplantation in Chronic Anterior Cruciate Ligament Reconstruction," *ESSKA 96*, (1996).

V. Bobic, "An Update on Arthroscopic Osteochondral Autograft Transplantation in ACL Reconstruction," *AOSSM 22nd Annual Meeting*, (1996).

V. Bobic, "Arthroscopic Osteochondral Autograft Transplantation in Anterior Cruciate Ligament Reconstruction: A Preliminary Clinical Study," *J Bone Joint Surgery* [BR], vol. 78–B: Supp. 1 (1996).

Mankin et al., Restoration of the Osteoarthrotic Joint, *J Bone Joint Surgery*, vol. 78–A, No. 1, pp. 1–2 (Jan. 1996).

J. Buckwalter, "New Methods of Treating Chondral Defects in the Knee" (undated).*

L. Hangody, "Autologous osteochondral mosaic–like graft technique for replacing weight–bearing cartilage defects," ESSKA 96, Budapest, Hungary (May 10–15, 1996).*

P. Albrecht–Olsen, T. Lind, G. Kristensen, B. Falkenberg, "Pull–out test after reinsertion of meniscus bucket–handle lesions with suture versus Biofix® tacks—an experimental study," *Scandinavian Orthopedic Association, Proceedings of the 47th Assembly*, Supplementum No. 260, vol. 65, Jun. 1994, p. 17.

M. Roffman, "Autogenous grafting for an osteochondral fracture of the femoral condyle," *Orthopaedica Scandinavica*, vol. 66, No. 6, Dec. 1995, pp. 571–572.

John C. Garrett; "Osteochondritis Dissecans"; Clinics in Sports Medicine; vol. 10, No. 3; Jul. 1991; pp. 569–593.

H.K. Outerbridge, et al; "The Use of a Lateral Patellar Autologous Graft for the Repair of a Large Osteochondral Defect in the Knee"; The Journal of Bone and Joint Surgery; vol. 77–A, No. 1; Jan. 1995; pp. 65–72.

G.E. van Dyk, et al; "Cancellous Bone Grafting of Large Osteochondral Defects: An Experimental Study in Dogs"; Arthroscopy: The Journal of Arthroscopic and Related Surgery; vol. 14, No. 3; Apr. 1998; pp. 311–320.

Innovasive COR™ System, Innovasive Devices, Inc., Jan. 1997.

Innovasive COR™ System: An Arthroscopic Technique for Harvesting and Transplanting Bone Grafts, Innovasive Devices, Inc., pp. 1–4, Sep. 1996.

* cited by examiner

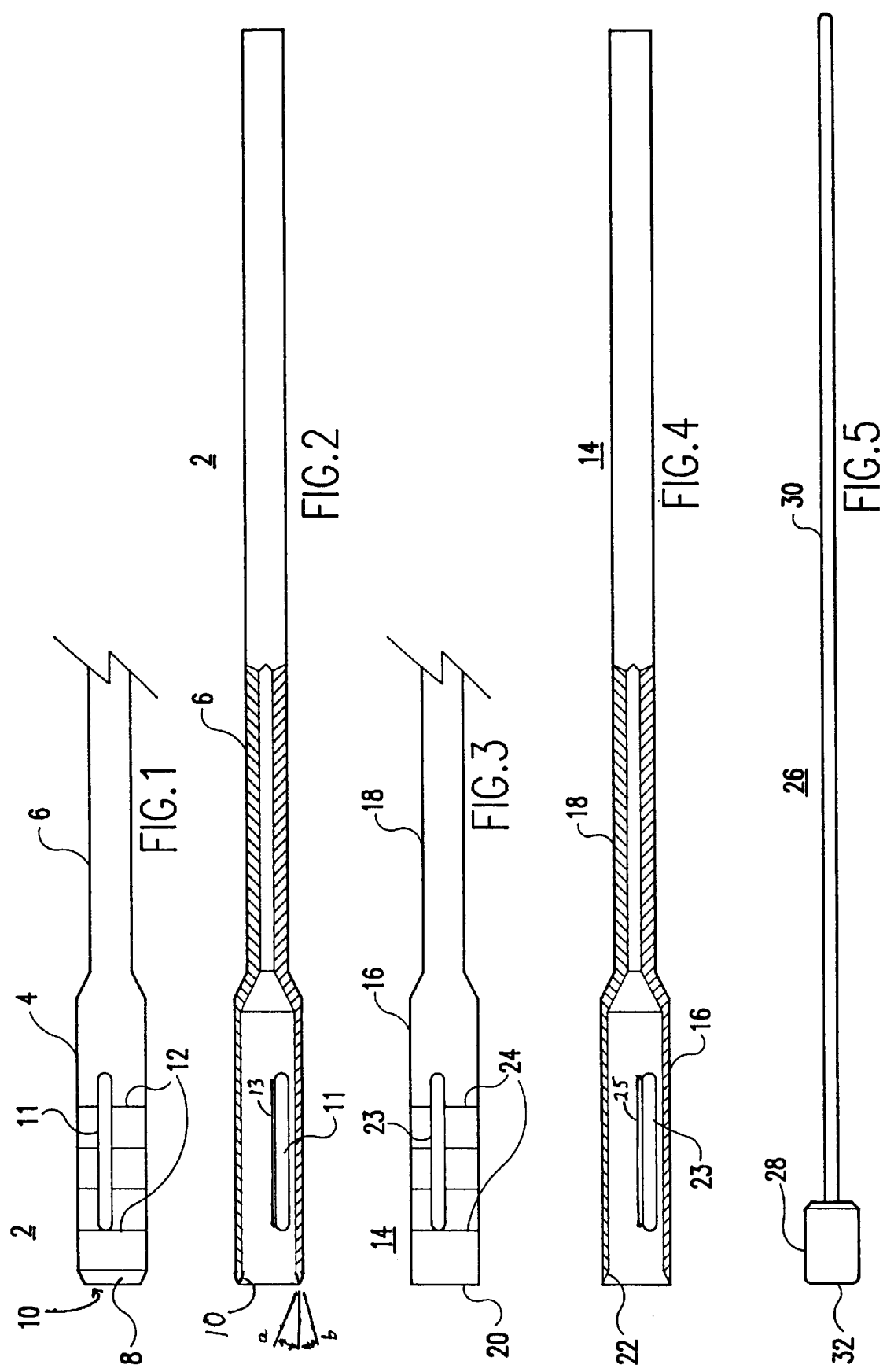

APPARATUS FOR OSTEOCHONDRAL AUTOGRAFT TRANSPLANTATION

This application is a continuation-in-part of allowed application Ser. No. 08/885,752, filed Jun. 30, 1997, now U.S. Pat. No. 5,919,196, which is a continuation-in-part of application Ser. No. 08/801,635, filed Feb. 18, 1997, now U.S. Pat. No. 5,785,714, which is a continuation of application Ser. No. 08/389,492, filed Feb. 16, 1995, now U.S. Pat. No. 5,603,716, the disclosures of which are incorporated by reference herein. This application also claims the benefit of U.S. Provisional Application Serial No. 60/024,045, filed Aug. 16, 1996, the disclosure of which is incorporated herein by reference.

BACKGROUND OF THE INVENTION

1. Field of the Invention

The present invention relates to the surgical treatment of chondral defects and, more specifically, to apparatus for autogenous or allograft transplantation of articular cartilage/bone cores in knees having chronic anterior cruciate ligament (ACL) deficiency, or isolated articular defects.

2. Description of the Related Art

As shown in FIG. 1, windows 11 and depth markings 12 are provided on the tube of the donor site harvester along the portion of the tube where the bone core is received to assist the surgeon during insertion of the harvester into the bone at the donor site. A longitudinal marking line (not shown) provided at the top of each harvester facilitates core alignment in the recipient socket.

Chondral defects of the femoral condyles are widely recognized indications which comprise approximately 5% of all knees undergoing arthroscopy. Treatment, however, is difficult and controversial. In earlier known methods, meniscal pathology was treated, and the ACL was reconstructed, but the chondral lesion usually was left untreated. This approach leads to lesion enlargement and ultimately an advancing arthritic condition.

A protocol of arthroscopic osteochondral autograft transplantation for repairing chondral defects has been developed and tested in knees having chronic ACL deficiency by Vladimir Bobić, as reported in Arthroscopic Osteochondral Autograft Transplantation In ACL Reconstruction: A preliminary clinical study; Knee Surgery, Sports Traumatology Arthroscopy (1996), incorporated herein by reference.

The transplantation procedure, which is intended to prevent further joint degeneration and possible development of osteoarthrosis, involves selecting donor sites for osteochondral cores, capped with intact cartilage, prior to notchplasty. Donor sites are selected along the anterolateral and superior aspect of the notchplasty area, or on the superolateral and anterolateral aspect of the lateral femoral condyle in the non-weightbearing area above the sulcus terminalis. At the donor sites, multiple osteochondral cores 5 mm to 9 mm in diameter and 10 to 15 mm long, are harvested using tubular cutting instruments.

Recipient repair sites typically are located on the weight-bearing area of the medial and lateral femoral condyles. Full-thickness chondral defects, typically larger than 10 mm in diameter, and up to 20 mm, are selected for treatment. Recipient sockets at the repair sites are prepared, and the donor cores are transferred and press-fitted into the recipient sockets.

The transplantation procedure described above has various difficulties associated with it. For example, removing the osteochondral cores from the tubular cutting instruments is difficult. In addition, improvements are needed in the formation of the donor cores and recipient sockets, especially to facilitate depth control during harvest, as well as transplant removal and insertion. In general, improvements are required in the instrumentation and techniques available to perform the transfer procedure.

SUMMARY OF THE INVENTION

The present invention overcomes the deficiencies in the prior art by providing surgical instruments for performing osteochondral transplant procedures using a series of thin-walled (0.5 mm) cutting tubes. Osteochondral cores, made up of hyaline cartilage capping subchondral bone, are harvested, either autogenously or as allografts. The osteochondral cores, preferably 10 to 15 mm in length, are transplanted into sockets created in the defect to accept the transplanted core, or multiple cores, in a press-fit manner. The instruments allow the technique of the present invention to be carried out as either an open procedure or arthroscopically. Determinations regarding the protocol used will be based, for example, on the location, geometry, and extent of the chondral defect and the harvest sites.

The instrumentation of the present invention includes a series of core harvesters. The harvester of the present invention preferably includes a hollow tube having a distal cutting edge and a cannulated handle attached proximally. Within each core harvester, a collared pin is disposed slidably to facilitate removal of the harvested osteochondral core. The collared pin acts as a plunger to urge the harvested core from the lumen of the core harvester tube, and preferably has a concave face for enhanced biomechanical contact with the curved surface of the harvested core.

Preferably, two types of harvesters are provided: a donor harvester for obtaining donor osteochondral cores, and a recipient site harvester for forming recipient sockets at repair sites.

Advantageously, the inner diameter of the donor harvester is equal to the outer diameter of the recipient site harvester. The outer diameters differ by 1 mm to accommodate the 0.5 mm wall thickness. The thin walls minimize bone and tissue damage.

The harvesters are provided in a range of sizes. To assist in harvesting to the proper depth, markings are provided on the instruments. The markings preferably are located on the outer surface of the harvester tubes for direct visual alignment with the surface of the tissue being harvested. Slotted windows are provided through the side walls of the tube to allow visualization of the harvested osteochondral core within the lumen of the harvester tube, allowing for visual confirmation of core length and surface geometry, for example, and for visual confirmation of depth during insertion.

The two types of bone harvesters can be distinguished by the formation of the sharp, distal cutting edge. On the donor graft harvesters, the distal cutting edge preferably is formed as a dual bevel, such that the cutting edge is formed by two 10° slanted surfaces sloping distally from the inner and the outer surfaces. The two bevels meet to form the cutting edge. Accordingly, the acutely-angled cutting edge is formed at the junction between the outer beveled surface and the inner beveled surface of the harvester tube wall. Accordingly, the donor harvester slightly compacts the bone core during harvesting.

On the recipient site harvesters, the distal cutting edge preferably is formed with a bevel which is formed by a slanted surface that slopes distally and outward from the central axis, from the inner surface to the outer surface of the harvester tube wall. Accordingly, the acutely-angled cutting edge is formed between the inner, beveled surface and the outer surface of the harvester tube wall.

The two harvesters cooperate for precise correspondence in size between the donor graft and the recipient site. Advantageously, the dual bevel on the donor harvester provides a slight compression, which results in a desirable press fit of the donor upon insertion into the correspondingly-sized recipient socket. Correct sizing avoids problems associated with an improper fit of the graft in the recipient site, including over-compression or insufficiency of the repair.

According to a preferred method, the donor harvester is inserted into a tube harvester driver/extractor and placed over the selected hyaline cartilage harvest site. The donor harvester is placed flush with the articular cartilage surface and impacted, using a mallet for example, to a selected depth of approximately 10 to 15 mm. After complete insertion to the selected depth, the driver/extractor is twisted and gently rocked to fracture the cancellous base for removal of the osteochondral core.

A recipient site is prepared with a recipient site harvester using a similar method. Alternatively, recipient sockets can be formed using various techniques, such as by drilling. The donor core preferably is pressed into the recipient site directly from the donor harvester.

Prior to insertion, size correlation between the donor core and the recipient site is provided by using a graft sizer and an alignment stick. The depth of the recipient site is determined using the alignment stick. If the graft osteochondral core is too long, adjustment of the core length or the length of the recipient site can be effected accordingly.

Using the driver/extractor, the donor osteochondral core is advanced with the collared pin so that the distal end of the core is flush with the end of the cutting edge of the harvester tube. As a manual aid to insertion depth control, the collared pin is sized so that the proximal end comes flush with the proximal end of the harvester handle when the distal end of the collared pin is 1 mm recessed from the cutting edge of the cutting end of the bone harvester. Accordingly, nearly-flush, anatomical insertion of the cartilage/bone core can be obtained without direct visual observation, and over-insertion is avoided.

In an alternative arrangement, the harvested donor bone graft is pressed using the collared pin into a rigid, transparent graft transfer tube, preferably made of plastic. The graft transfer tube allows visualization of the transfer procedure and provides increased confidence in performing the graft procedure.

After insertion, the osteochondral core insert is brought flush anatomically using a sizer/tamp. The graft is pressed with the sizer/tamp such that the surface of the graft comes into flush alignment with the normal articular cartilage surrounding the recipient repair site.

Although the instruments and techniques are described herein in connection with a specific autograft application in the ACL-deficient knee, they can be applied to ACL-normal knees, for treatment of joints other than the knee, and for xenogenous procedures. In addition, indications for the instrumentation and techniques of the invention can be extended to include other treatments, such as, for example, osteochondritis dissecans, allograft transplantation, bone grafting, graft fixation, and focused bone core biopsy.

Other features and advantages of the present invention will become apparent when the following description is read in conjunction with the accompanying drawings.

BRIEF DESCRIPTION OF THE DRAWINGS

FIG. 1 is a partial side view of a donor graft harvester according to the present invention.

FIG. 2 is a cut-away side view of the donor graft harvester of FIG. 1.

FIG. 3 is a partial side view of a recipient site harvester according to the present invention.

FIG. 4 is a cut-away side view of the recipient site harvester of FIG. 3.

FIG. 5 is a side view of a collared pin according to the present invention.

DETAILED DESCRIPTION OF THE PREFERRED EMBODIMENTS

Figure 6:
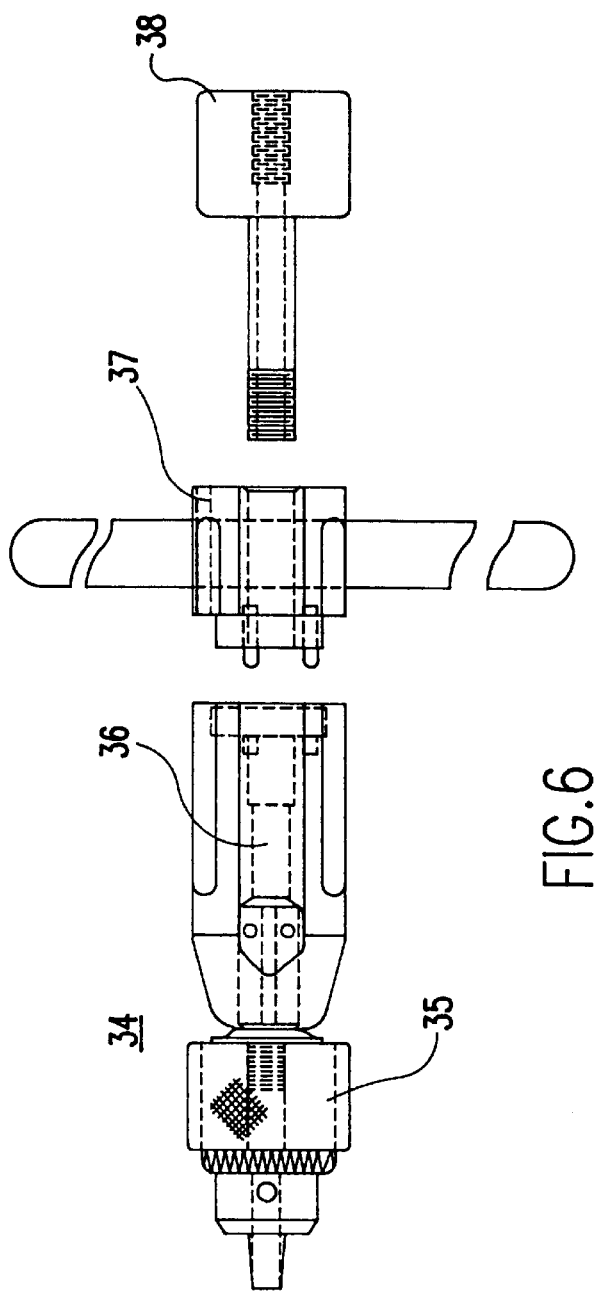
FIG. 6 is a cut-away side view of a driver/extractor handle according to the present invention.

Referring to FIGS. 1 and 2, a donor graft harvester 2 is shown. The donor graft harvester includes a hollow tube 4 attached to an elongated cannulated proximal end 6.

The graft harvester tube has a sharp cutting edge formed on the distal end thereof. The sharp edge is formed by a dual-bevel formed by surfaces 8 and 10. Surface 8 slopes inward distally from the outer surface toward the inner surface of tube 4 at an angle a of 10°. Surface 10 slopes outwardly from the inner surface at an angle b of 10°. Accordingly, the cutting edge is offset slightly (approx. 0.002"–0.003") from the inner surface of the donor harvester lumen. As a result, the harvested bone core is slightly compacted, to improve the strength and subsequent bone growth regeneration of the implanted core.

The donor harvester preferably is provided in a range of sizes. Accordingly, the inner diameters of hollow tubes 4 are, for example, 5, 6, 7, 8, and 9 millimeters. The walls of the harvester tubes are typically 0.5 millimeter thick. The thin walls minimize bone and tissue damage.

As shown in FIG. 1, windows 11 and depth markings 12 are provided on the tube of the donor site harvester to assist the surgeon during insertion of the harvester into the bone at the donor site. A longitudinal marking line (not shown) provided at the tip of each harvester facilitates core alignment in the recipient socket.

Windows 11 allow for arthroscopic confirmation of donor bone plug extraction prior to complete removal of the donor harvester, as discussed below. In addition, windows 11 allow a comparison of overall core length between donor and recipient cores. Windows 11 also allow visual control of core insertion depth by calibrating the collar and tube laser marks. Also, windows 11 provide increased surface friction between the tube and the osteochondral core to ensure core extraction, especially at lengths over 10 mm. To increase surface friction for removal and retention of the harvested core, at least a portion of one edge 13 of one of the windows 11 is coined into the inner lumen of the cutting tube.

The harvester has a sharp cutting edge 20 formed on the distal end of tube 16. The sharp edge is formed by a beveled surface 22 sloping outward distally from the inner surface to the outer surface of tube 16. See FIG. 4.

The recipient site harvester also is provided in a range of sizes. Accordingly, the outer diameters of hollow tubes 16 are, for example, 5, 6, 7, 8, and 9 millimeters, in correspondence with the inner diameter of the associated donor graft harvester described above. As with the donor harvester, the walls of the recipient harvester tubes are thin, and windows 23 and depth markings 24 are provided on the tube, in a manner and for reasons similar to those described above with respect to donor harvester 2. Preferably one edge 25 of one of the windows 23 is coined similarly to edge 13 described above for enhanced retention of the harvested core.

Referring to FIG. 5, a collared pin 26 according to the present invention is shown. Pin 26 is made up of a collar 28 disposed on a distal end of an elongated shaft 30. The surface 32 at the distal end of collar 28 is smooth and concave for enhanced biomechanics and to prevent damage to the cartilaginous surface of the graft core, similar to that of the sizer/tamp, described below. The preferred spherical radii of the concavity for the distal end surfaces for various instrument sizes are set forth in the following Table I:

TABLE I

| Size | Diameter | Radius [metric] |
|---|---|---|
| 5 mm | .151 [3.84] | .109 [2.74] |
| 6 | .191 [4.85] | .229 [5.82] |
| 7 | .230 [5.84] | .385 [9.78] |
| 8 | .269 [6.83] | .580 [14.73] |

TABLE I-continued

| Size | Diameter | Radius [metric] |
|---|---|---|
| 9 | .309 [7.85] | .831 [21.11] |
| 10 | .348 [8.84] | 1.090 [27.69] |
| 11 | .387 [9.83] | 1.410 [35.81] |
| 12 | .427 [10.85] | 1.754 [44.55] |
| 13 | .466 [11.84] | 2.144 [54.46] |
| 14 | .506 [12.85] | 2.578 [65.48] |
| 15 | .545 [13.85] | 3.046 [77.37] |

Pin 26, having a collar 28 of appropriate size approximating the inner diameter of the harvester, is received within handle 6 of the donor graft harvester, or handle 18 of the recipient site harvester, prior to insertion of the respective harvester into the selected harvesting or donation site. Accordingly, the proximal shaft of pin 28 is inserted through hollow tube 4, 16, respectively, such that the collar is disposed within the tube prior to harvesting cores at the donor graft or recipient sites.

The proximal end of the pin extends beyond the proximal end of the harvester to an extent at least equal to the length of the tube, such that the harvested core can be removed easily from the lumen of the harvester tube by urging the collared pin distally to advance the harvested core. In this respect, the harvesters of the present invention are similar to the coring reamer of co-owned U.S. Pat. No. 5,423,823, the disclosure of which is incorporated herein by reference, and the bone harvester disclosed in co-owned U.S. Pat. No. 5,603,716.

Referring to FIG. 6, a tube harvester driver/extractor 34 according to the present invention is shown. Cannulated tube harvester driver/extractor 34 preferably is assembled of three sections including a chuck end 36, a removable T-shaped handle 37 and an impact end 38. Chuck 35 at the distal end of driver/extractor 34 secures onto the proximal end of harvesters 2, 14, and is cannulated to receive the proximal end of pin 26. Removable handle 37 is used to manipulate the driver/extractor assembly.

According to the inventive procedure, as described more fully below, impact end 38 is struck with a mallet to drive the harvester/driver assembly into the selected harvesting site. Upon removal of end 38 and handle 37, the proximal end of pin 28 of collared pin 26 is exposed for removal of the harvested cores from the harvester tubes, also set forth more fully below. Alternatively, the entire driver/extractor can be removed from the harvester prior to transfer.

Figure 7:
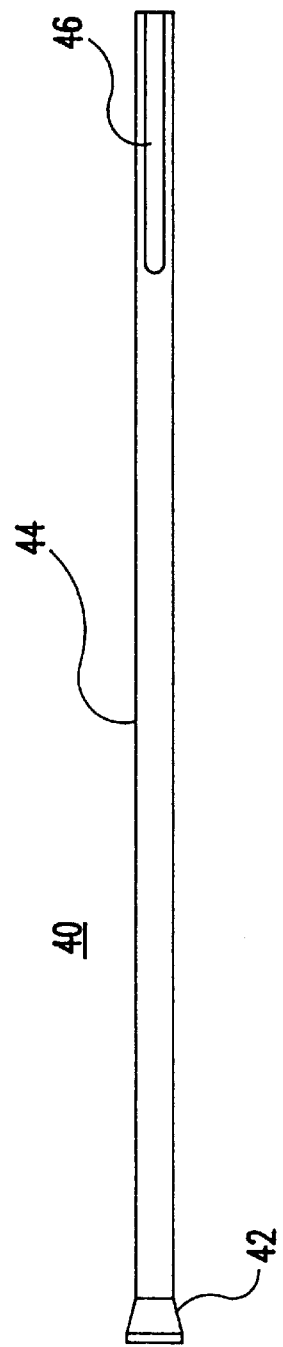
FIG. 7 is a side view of a graft sizer/tamp according to the present invention.

Referring to FIG. 7, a graft sizer/tamp 40 is shown. Sizer/tamp 40 has a tamp head 42 disposed on a shaft 44. Three flats 46 are formed on the proximal end so that sizer/tamp 40 can be chucked into driver/extractor 34. The core-contacting surface at the distal end of the sizer/tamp is smooth and has a spherical concavity, similar to that of the collared pin discussed above. The spherical concavity of the sizer/tamp differs from that of the collared pin in that the outer edge of the concavity extends to and coincides with the outer diameter of the sizer/tamp. In contrast, the outer diameter of the collared pin is radiused, and the outer edge of its spherical concavity is set in slightly from the radiused edge. Table II sets out the preferred spherical radii of the concave surface for various sizes of the sizer/tamps, as follows:

TABLE II

| Size | Diameter | Radius [metric] |
| --- | --- | --- |
| 5 mm | .197 [5.0] | .29 [7.4] |
| 6 | .236 [6.0] | .46 [11.7] |
| 7 | .276 [7.0] | .68 [17.3] |
| 8 | .315 [8.0] | .94 [23.9] |
| 9 | .354 [9.0] | 1.22 [31.0] |
| 10 | .394 [10.0] | 1.55 [39.4] |

The method according to a preferred embodiment of the present invention will be described with reference to FIGS. 8 through 18.

Figure 8:
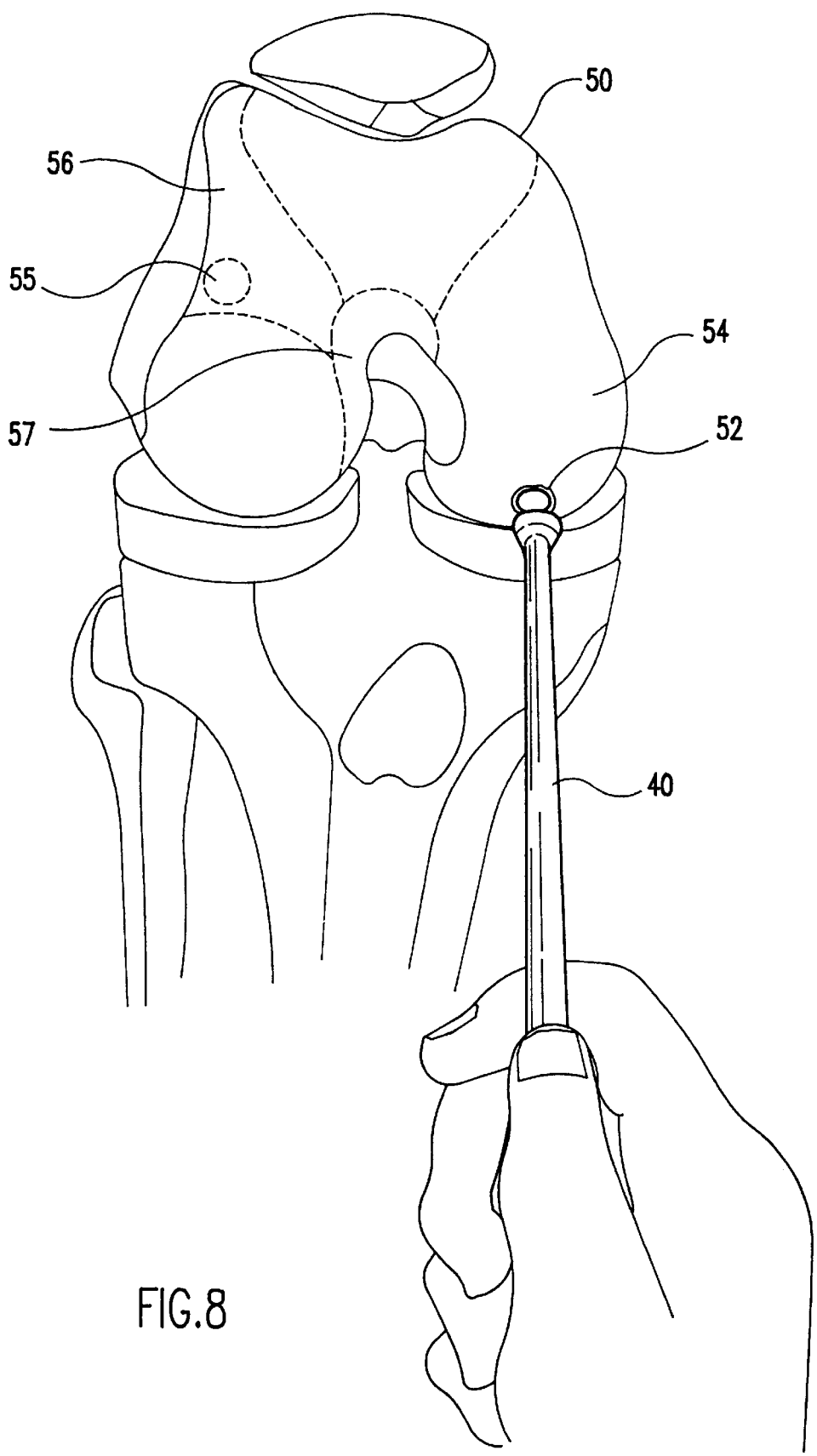
FIG. 8 illustrates chondral defect size determination and surgical planning according to the present invention.

Referring to FIG. 8, an anterior aspect of a right knee 50 is shown diagrammatically. A chondral defect 52 in femoral condyle 54 is inspected arthroscopically and the extent of the lesion assessed with sizer/tamp 40. Tamp 40 has the appropriate 5, 6, 7, 8, or 9 mm diameter Delrin head, which correlates with the diameter of the cutting tube harvesters.

A tamp 40 of appropriate size also can be used to evaluate potential harvest donor sites, such as site 55, in an area 56 along the outer edges of the non-articulating margin of the lateral femoral condyle above the sulcus terminalis or directly adjacent to the superolateral margin 57 of the intraarticular notch.

Surgical planning with respect to transferring single or multiple osteochondral cores, appropriate osteochondral core diameter, and whether to proceed with an arthroscopic versus an open procedure must be assessed prior to further surgical transplantation intervention. Selection and size of single or multiple core grafts should be based on harvest site accessibility and the convex/concave surface shape relationship of the available donor and recipient sites.

The appropriate, single-use tube harvester set of one-each donor harvester 2 and one-each recipient harvester 14 with respective collared pins 26 is selected based on defect and harvest site measurements. The donor tube harvester is selected to have an outer diameter 1 mm larger than the recipient tube harvester. The inner diameter of the donor tube is thus equal to the recipient outer tube diameter to assure a press fit fixation of the donor core in the recipient site. Tube harvester sets consist of 5 and 6 mm, 6 and 7 mm, 7 and 8 mm, 8 and 9 mm, or 9 and 10 mm sizes.

Figure 9:
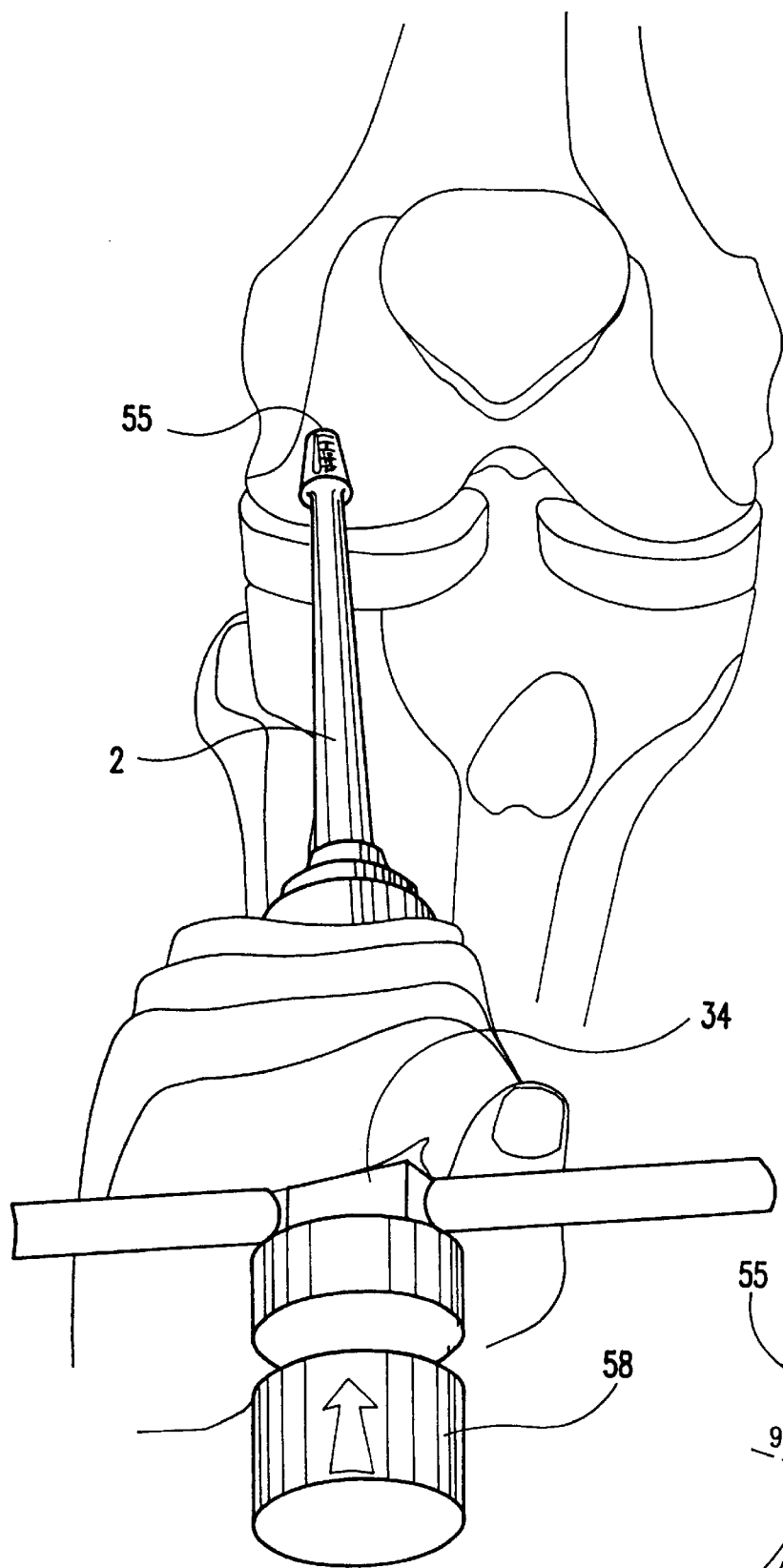
FIG. 9 illustrates donor harvester tube impaction according to the present invention.
Figure 10:
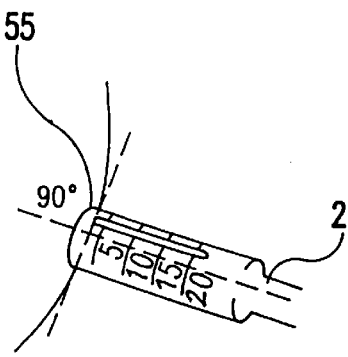
FIG. 10 illustrates proper alignment of the donor harvester tube according to the present invention.

Referring to FIG. 9, the donor tube harvester 2 of the appropriate diameter and labeled "DONOR" is inserted fully into the tube harvester driver/extractor 34 (see FIG. 6) and placed over the hyaline cartilage harvest site 55. Care must be taken to adjust the insertion and/or knee flexion angle so that the tube harvester end is flush with the articular cartilage prior to impaction. See FIG. 10. The tube harvester is driven into subchondral bone with a mallet 58 to a depth of approximately 15 mm. Care should be taken not to rotate the harvester during insertion so as to avoid damaging the core to be harvested.

During an arthroscopic procedure, a slotted cannula (not shown) may be used to facilitate larger diameter tube harvester insertion into the joint. After insertion, the slotted cannula is pulled back along the tube harvester shaft and removed sideways through the slot to increase intraarticular visualization, tube harvester mobility, and fluid distension.

Figures 11, 12:
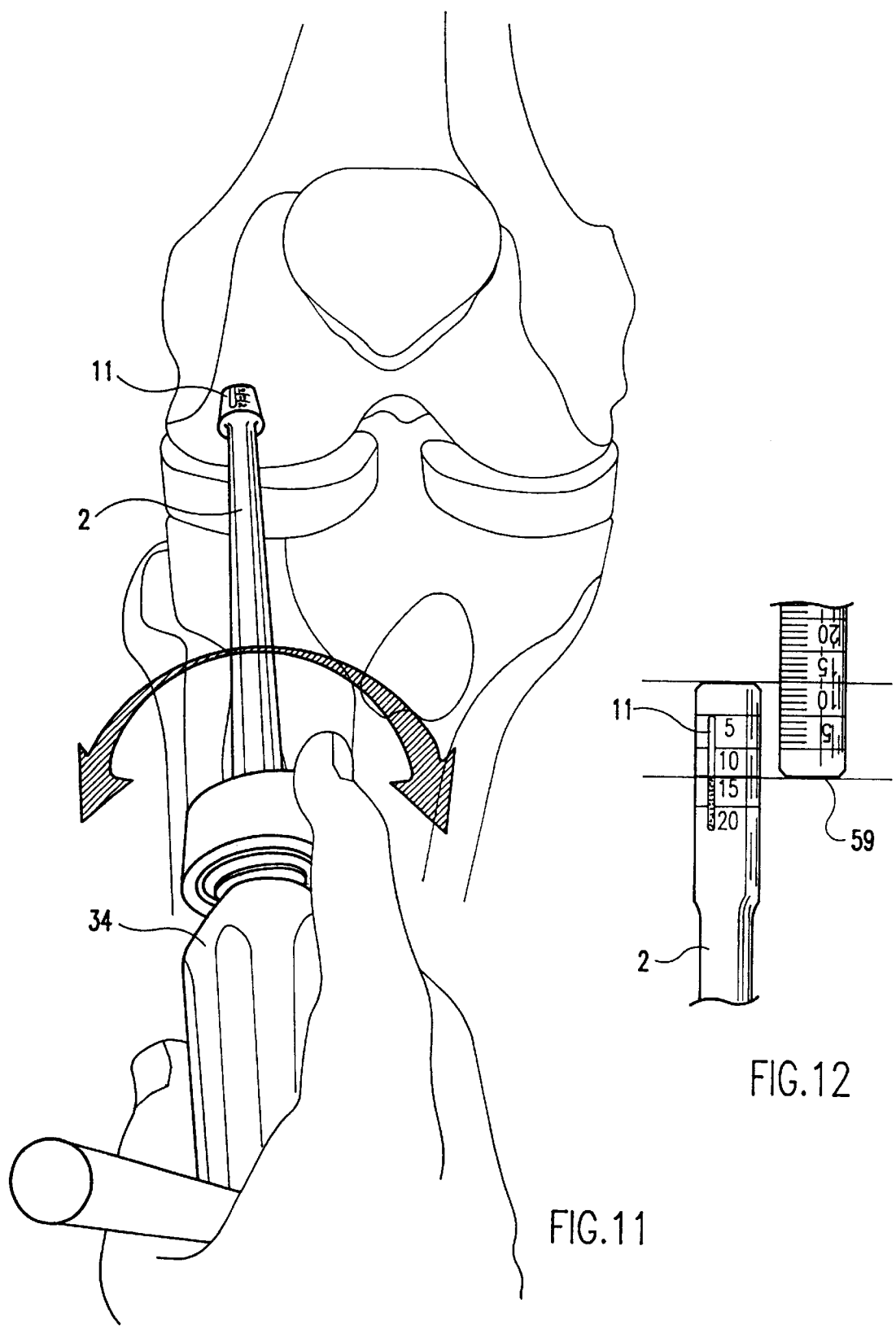
FIG. 11 illustrates donor core harvesting according to the present invention.
FIG. 12 illustrates bone core sizing according to the present invention.

Referring to FIG. 11, driver/extractor 34 is rotated, preferably about 90° clockwise, about 90° counter-clockwise, and then gently rocked, superior and inferior, to fracture the cancellous base for removal of the osteochondral core. Donor tube harvester 2 is then retrograded from the donor site with the harvested core captured within the tube.

The harvested core can be visualized through windows 11 to verify that the core has been captured successfully within the harvester. If rotation and extraction of the tube harvester should fail to capture the core for removal, reinsertion and further impaction of the tube harvester up to 20mm with subsequent rotation and extraction steps may be indicated.

Once the donor core is removed, its length and hyaline cartilage thickness can be seen through the windows 11 in the harvester, as shown in FIG. 12. Accurate measurements can be obtained using a calibrated alignment stick 59, discussed further below. After extraction, the donor tube harvester 2 and the captured core are removed from the driver/extractor and placed in a secure, sterile holding area.

Alternatively, the core can be pressed out of the harvester into a transfer tube 70 (see FIG. 19A), preferably formed of a substantially transparent material and open at opposite ends. The sufficiency of the core then can be verified visually. The transfer tube then is used in place of the donor harvester to insert the core into the recipient socket.

Figures 13, 14:
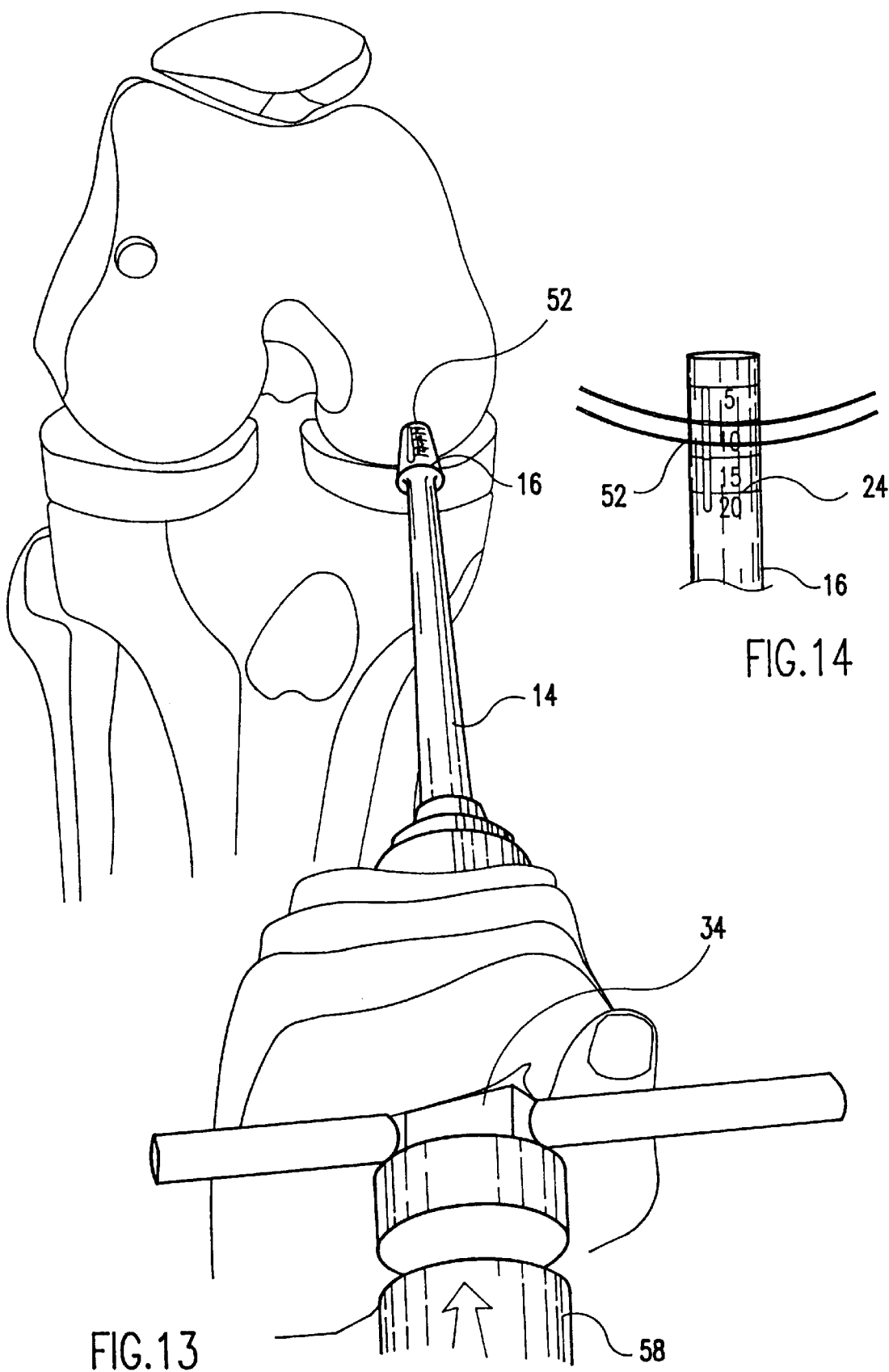
FIG. 13 illustrates recipient socket harvester impaction according to the present invention.
FIG. 14 illustrates recipient socket depth control according to the present invention.

Referring to FIG. 13, the appropriately-sized tube harvester 14 labeled "RECIPIENT" and collared pin 26 from the tube harvester set are inserted fully into the tube harvester driver/extractor 34. If a single core transfer is indicated to replace the surface of the defect 52, recipient tube harvester 14 is placed over the defect and driven into the subchondral bone with mallet 58. Again, rotation of the recipient harvester is avoided during insertion of the harvester, as noted above with respect to insertion of the donor harvester. The preferred depth of about 13 mm. is determined with the tube harvester millimeter depth markings 24 on the outer surface of tube 16, as shown in FIG. 14.

Care should be taken to select the proper insertion angle and knee flexion to allow the tube harvester to sit flush to the chondral surface prior to impaction. If multiple core transplantation is desired, the tube harvester is placed over the appropriate quadrant in the defect.

Also, during socket creation, attention to maintaining the harvester at a 90° angle to the articular surface, in both the sagittal and coronal planes, is very important to obtain a flush transfer. See FIG. 14.

If angled harvesting must be performed due to anatomical obstruction to 90° placement of tube harvester flush with hyaline cartilage, a longitudinal marking line (not shown) at the tip of each tube harvester should be rotated to align with the leading cutting edge into cartilage during donor core harvesting. Recipient harvesting should be performed at an angle as close as possible to the angle used during donor core harvesting. This facilitates close approximation of the angled hyaline cartilage donor surface with the surrounding cartilage of the angled recipient socket by aligning the longitudinal marking line and leading cutting edge of the donor tube against the recipient socket rim during donor core insertion.

Figure 15:
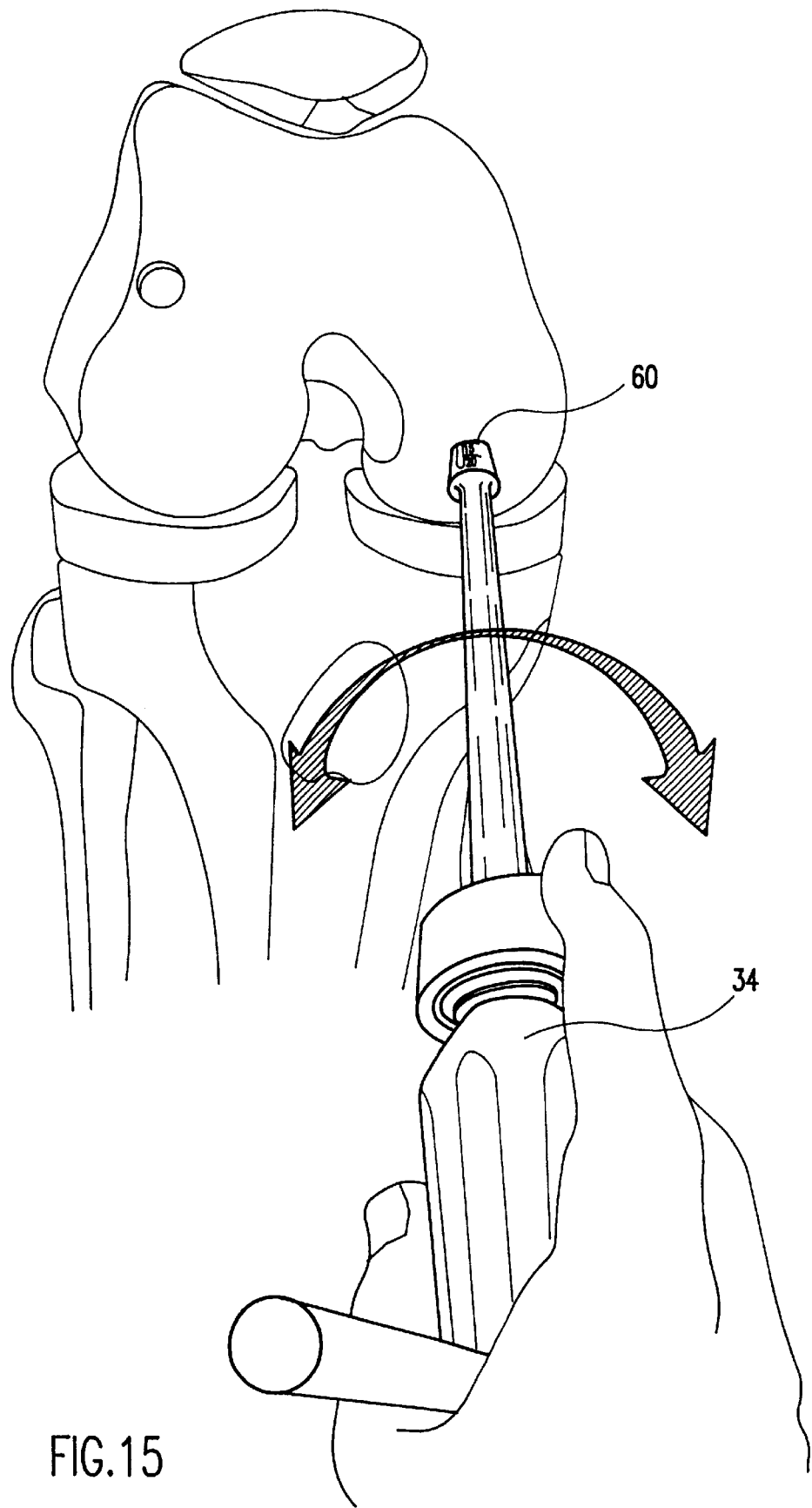
FIG. 15 illustrates recipient socket core extraction according to the present invention.

Referring to FIG. 15, after sufficient tube harvester depth is determined, the tube harvester driver/extractor 34 is rotated and gently rocked, as with the donor harvester above, to fracture the cancellous bone at the distal end of the tube. Extraction of the tube harvester and core can be facilitated by simultaneous counter rotation and extraction of the tube driver so as to form recipient socket 60.

After extraction of the harvester and its captured osteochondral core, the lengths of the donor and recipient cores can be compared directly by placing the donor and recipient harvesters side by side. The harvested cores can be viewed through windows 11 and 23 in the donor and recipient harvesters, respectively. Adjustments to the length of the harvested autograft donor core can be made accordingly. Preferably, the distal end of the donor core is smoothed prior to insertion into the recipient site.

Figure 16:
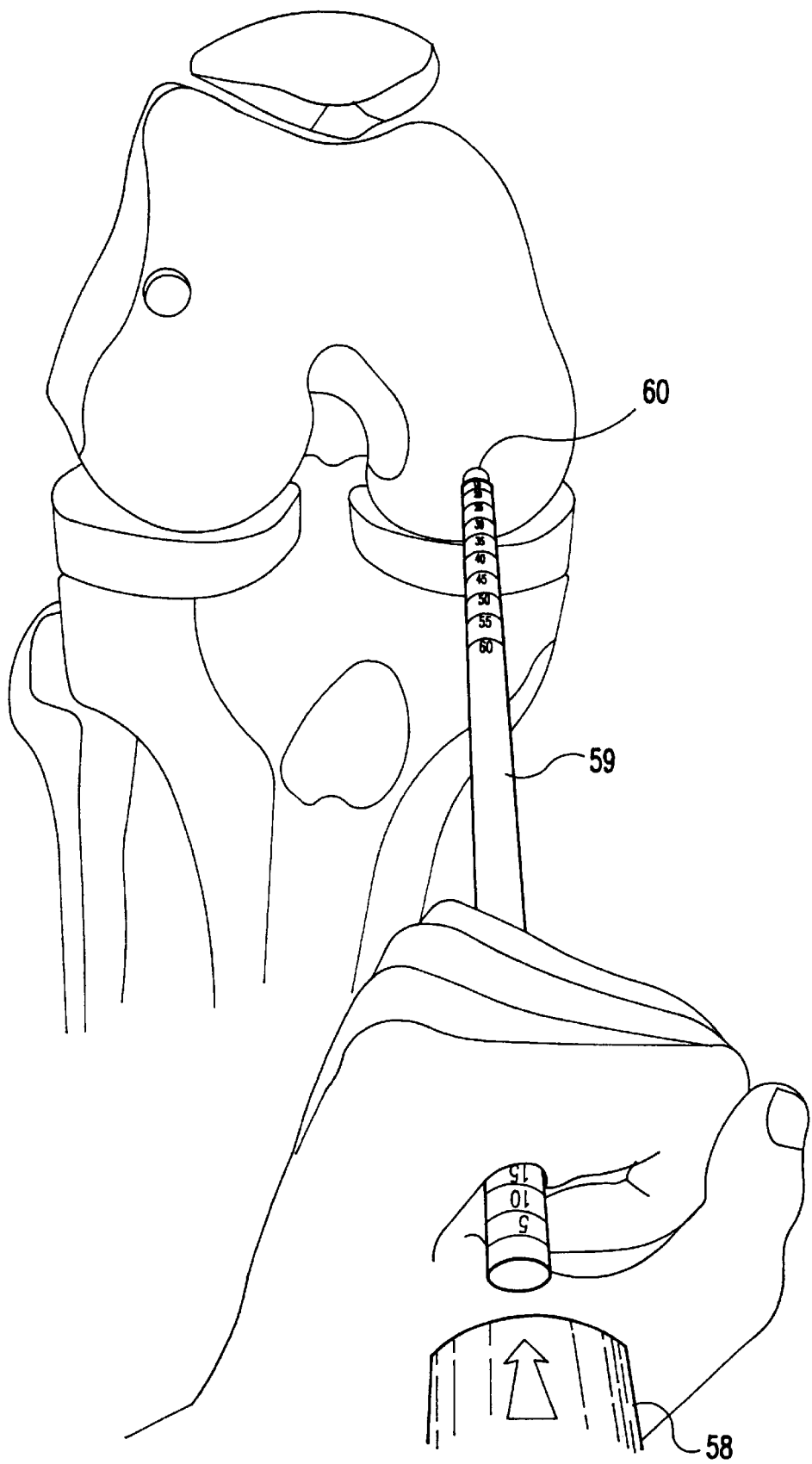
FIG. 16 illustrates recipient socket sizing and preparation according to the present invention.

Referring to FIG. 16, calibrated alignment stick 59 of an appropriate diameter can be used to measure the depth of recipient socket 60. The alignment stick also can align correctly the angle of the recipient socket with respect to the position of an insertion portal when an arthroscopic approach is used. Advantageously, the alignment stick also can be used to fine tune the recipient socket length as desired to match the length of the donor core. Accordingly, alignment stick 59 is impacted with mallet 58 until the desired depth is achieved.

For insertion of the autograft or allograft core, the recipient tube harvester 14 is replaced with the 1 mm diameter-larger donor tube harvester 2 and collared pin with the captured autograft core. The donor tube harvester is inserted fully into the tube harvester driver/extractor 34.

Figures 17, 18:
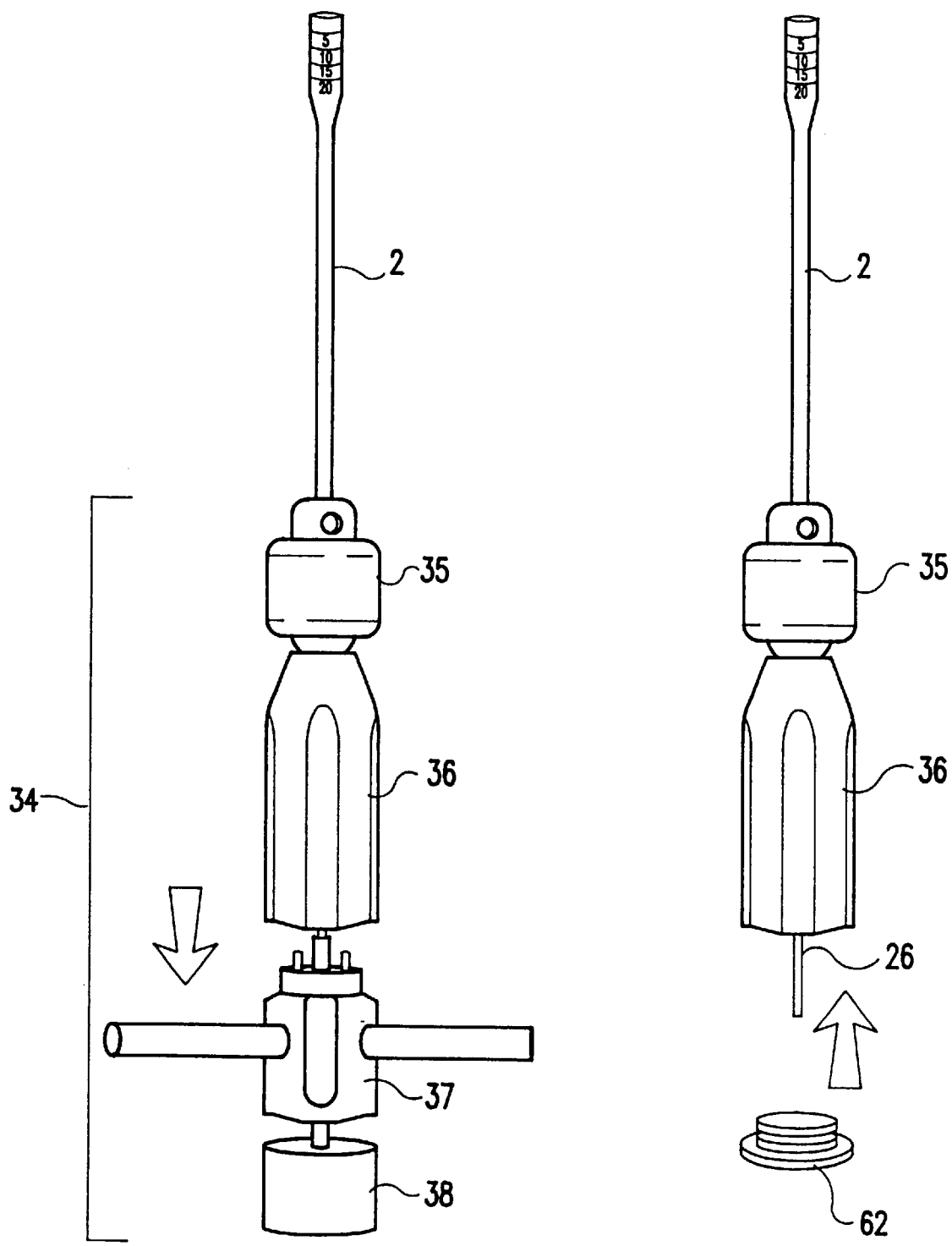
FIG. 17 illustrates assembly preparation of the driver/extractor of the present invention.
FIG. 18 illustrates preparation of the driver/extractor and donor core harvester for insertion in the recipient site according to the present invention.

Referring to FIGS. 17 and 18, after donor tube harvester 2 reinsertion into the driver/extractor 34, the driver/extractor impaction cap 38 is unscrewed and the T-handled midsection 37 is removed. Accordingly, the proximal end of collared pin 26 is exposed, which is used to advance the core directly into the recipient socket 60.

A stainless steel pin calibrator 62 is applied onto the open handle end for protection during further impaction, to maintain alignment of the collared pin, and to provide mechanical control of the bone core insertion. The pin calibrator preferably has an O-ring that press fits into the handle, and a small hole in the center that is threaded, so that the calibrator can be pulled out of the handle with a threaded retriever.

Figures 19, 20:
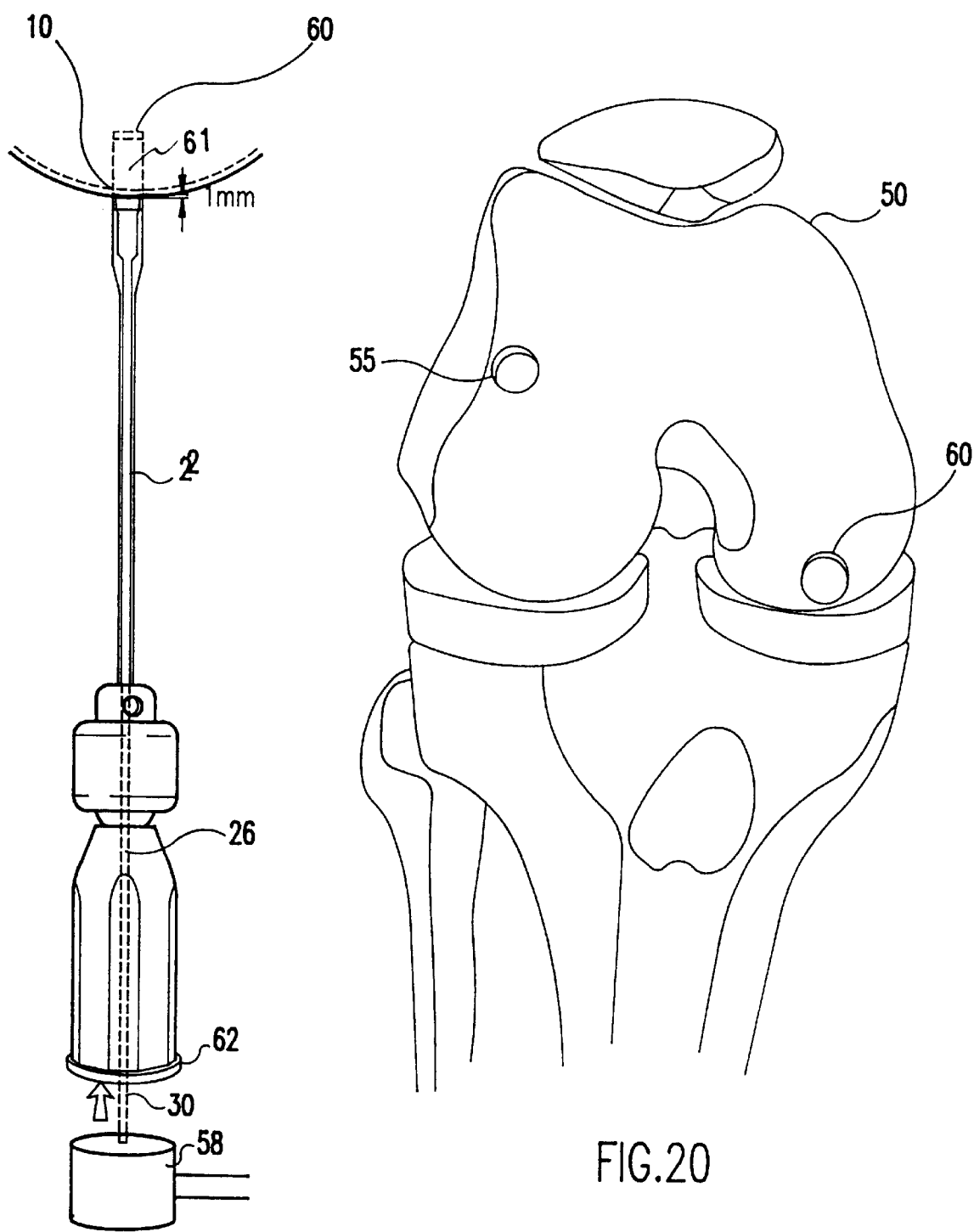
FIG. 19 illustrates donor core insertion according to the present invention.
FIG. 20 illustrates insertion of the donor core according to the present invention.

As shown in FIG. 19, the distal end of donor harvester 2 is inserted into recipient site 60. The beveled surface 10 helps to guide the harvester at the recipient site and assists in providing a secure fit and alignment of the donor harvester. A mallet is used to tap lightly onto the proximal end of shaft 30 of collared pin 26 to drive the core into the recipient socket 60 while maintaining stable positioning of the harvester tube and knee flexion angle.

The core is advanced so that 1 mm of core remains proud, as shown in FIGS. 19 and 20. Accordingly, the collared pin 26 is advanced until the end of the pin is flush with the pin calibrator 62. The predetermined length of the collared pin is designed to advance the bone core so that 1 mm of the graft will be exposed outside the recipient socket when the pin is driven flush with the end of the proximal face of the pin calibrator. Control of the core insertion also can be obtained by visualizing the core and collared pin advancement through windows 11 in the side of the harvester.

Figure 19A:
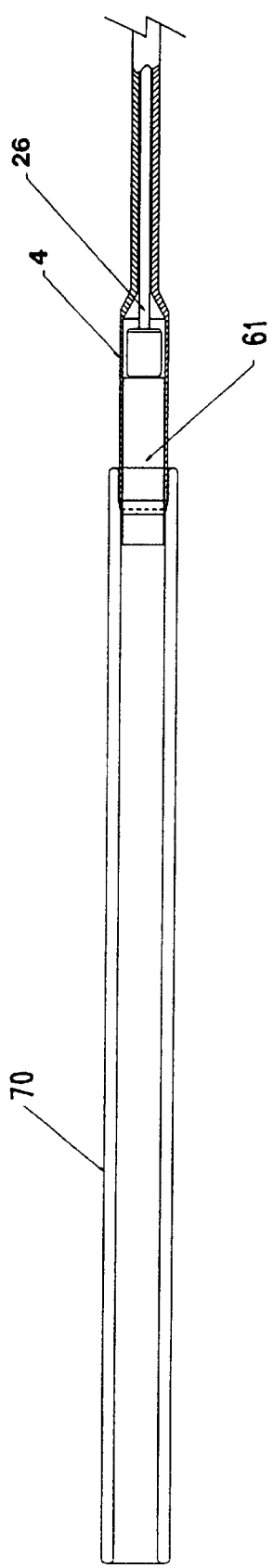
FIG. 19A illustrates donor core insertion using a transfer tube according the present invention.

Alternatively, referring to FIG. 19A, the harvested donor bone core is inserted using transparent transfer tube 70. Accordingly, the flared end of transfer tube 70 is placed over the distal end of cylinder 4 of donor harvester 2 holding donor graft 61. Advantageously, the graft can be visualized during insertion through transparent transfer tube 70. After insertion of the graft, and removal of the transfer tube, further adjustments to the graft insertion can be made using graft sizer/tamp 40.

Advantageously, incomplete insertion of the core avoids driving the core too far, which could result in a counter-sunk cartilage surface, requiring further invasive steps to pull back the core so as to be flush to surrounding articular cartilage. Over-insertion also is prevented by proper recipient socket preparation using the alignment stick, as set forth above.

Figures 21, 22:
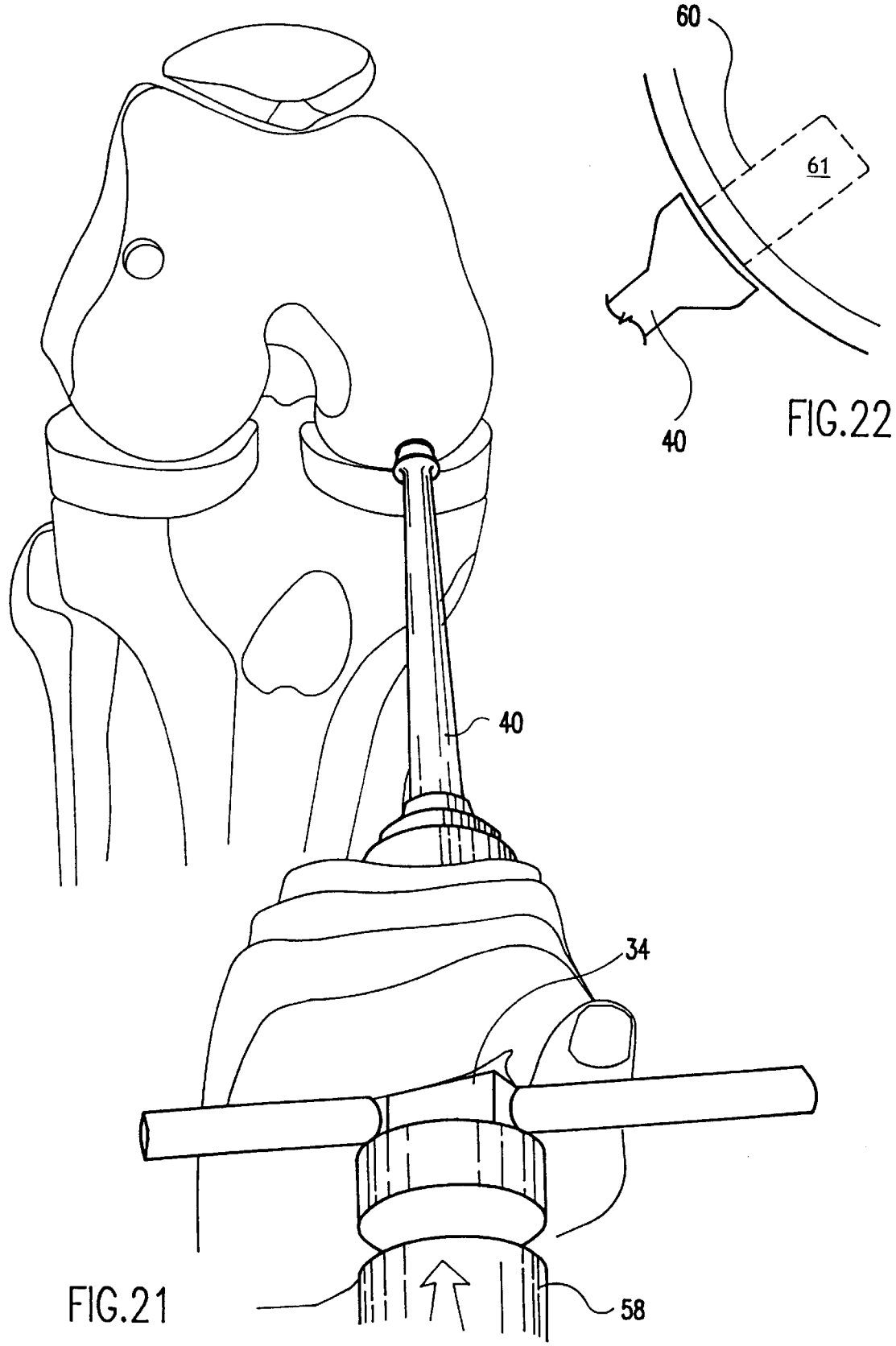
FIG. 21 illustrates final donor core seating according to the present invention.
FIG. 22 is a detailed closeup of the donor core seating step of FIG. 21.

Referring next to FIG. 21, sizer/tamp 40 is chucked into driver/harvester 34 for seating the core flush with the surrounding hyaline cartilage. According to one embodiment of the method of the present invention, the sizer/tamp diameter is at least 1 mm larger than the diameter of the core. As shown in FIG. 22, the larger diameter tamp provides complete control of proper core insertion depth flush to surrounding articular cartilage and eliminates any potential of overdriving.

Figure 23:
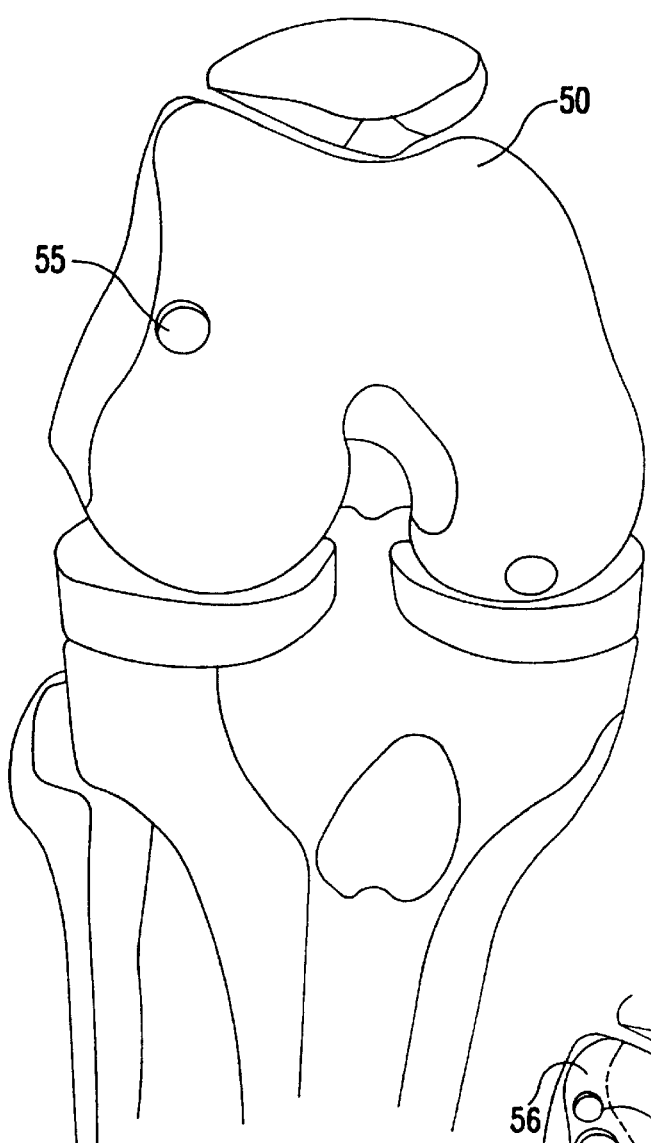
FIG. 23 illustrates a completed transplantation according to the present invention.

According to another embodiment of the inventive method, sizer/tamp 40 is the same as that used to determine the core size required, and is the same size as the osteochondral core. The tamp is used in an off-center position with respect to the core, so that the overhanging edge of the sizer/tamp encounters the surrounding cartilage area and prevents overinsertion of the bone core. The face of the core is seated flush with the surrounding cartilage surface, which is achieved by light tapping with the mallet 58. The completed transfer is shown in FIG. 23.

Figure 24:
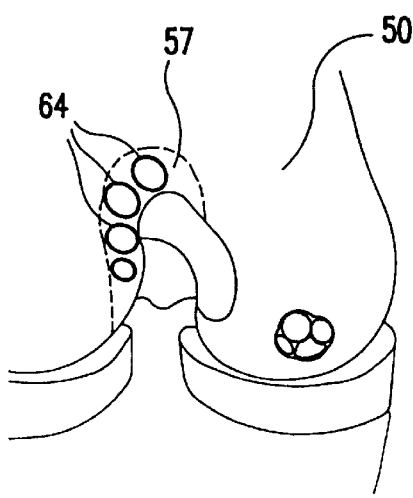
FIG. 24 illustrates multiple transfers according to the present invention.
Figure 25:
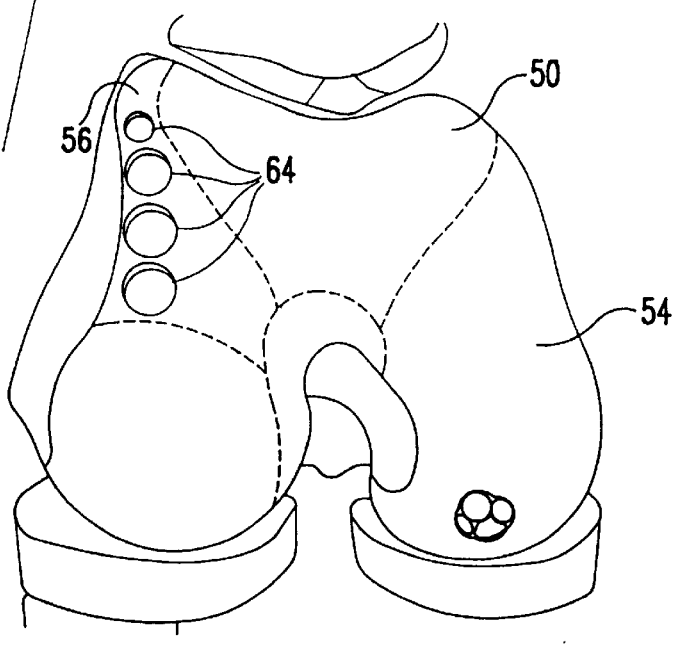
FIG. 25 illustrates multiple transfers according to the present invention.

When multiple cores of various diameters are to be harvested and transferred into specific quadrants of the defect, each core transfer should be completed prior to proceeding with further recipient socket creation. See FIGS. 24 and 25. This prevents potential recipient tunnel wall fracture and allows subsequent cores to be placed directly adjacent to previously inserted cores when desired.

Donor sockets 64 are routinely left open after harvesting and fill in with cancellous bone and fibrocartilage within 8 to 12 weeks. Alternatively, cancellous bone harvested from the defect may be inserted into donor sites, and should be tamped firmly into the donor socket with a sizer/tamper or alignment stick to compress the cancellous bone for enhanced fixation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. Apparatus for transplanting osteochondral cores in a joint, the apparatus comprising:

a cutting tube having a longitudinal axis and smooth sharp cutting edge on a distal end for cutting axially into bone without rotation of the cutting tube, a lumen having an inner diameter for receiving axially a cylindrical bone core harvested by the cutting edge, a slotted window in a side of the tube for viewing the cylindrical bone core received within the lumen, and an elongated cannulated proximal end;

a handle coupled to the cutting tube for twisting the cutting tube to remove the cylindrical bone core harvested by the cutting edge;

an impacting surface disposed proximally to the elongated cannulated proximal end and configured for receiving axial impacting forces for driving the cutting tube into the bone without rotation;

a pin having a distal end and a proximal end disposed slidably within the cutting tube, the pin having a collar disposed on the distal end of the pin and having a smooth blunt distal surface, for axially urging the harvested cylindrical bone core out of the cutting tube, the collar having a diameter approximating the inner diameter of the lumen, the proximal end of the pin having a diameter that is smaller than the diameter of the collar and being disposed slidably within the elongated cannulated proximal end of the cutting tube.

2. The apparatus of claim 1, wherein the window has an edge, and at least a portion of the edge is coined in toward the lumen for retaining the bone core within the lumen.

3. The apparatus of claim 1, further comprising a driver removably secured to the cutting tube.

4. The apparatus of claim 1, wherein the sharp cutting edge is formed by a dual bevel for compacting a bone core harvested with the apparatus.

5. The apparatus of claim 1, wherein the elongated cannulated proximal end of the cutting tube is open, and the proximal end of the pin extends through the open proximal end of the cutting tube.

6. The apparatus of claim 1, further comprising a transfer tube for receiving a core harvested with the cutting tube and pressed out of the cutting tube with the pin.

7. The apparatus of claim 1, wherein the slotted window extends along a portion of the tube in which the cylindrical bone core harvested by the cutting edge is received.

8. An apparatus for transplanting osteochondral cores in a joint, the apparatus comprising:
- a core-cutting tube, having a longitudinal axis and a smooth sharp cutting edge on a distal end for cutting axially into bone without rotation of the-cutting tube, a slotted window in a side of the tube for viewing a cylindrical bone core received within the tube, an elongated cannulated proximal end, and an inner diameter;
- a socket-cutting tube, having a longitudinal axis and a smooth sharp cutting edge on a distal end for cutting axially into bone without rotation of the cutting tube, an elongated cannulated proximal end, and an outer diameter equal to the inner diameter of the core cutting tube;
- a handle coupled to the respective cutting tubes for twisting the cutting tube to remove the cylindrical bone core harvested by the cutting edge;
- an impacting surface disposed proximally to each of the elongated cannulated proximal ends and configured for receiving axial impacting forces for driving the cutting tubes into the bone without rotation; and
- a pin disposed slidably within each of the cutting tubes, each pin having a distal end and a proximal end, each pin having a collar disposed on the distal end of the pin and having a smooth distal surface, the proximal end of the pin being disposed slidably within the elongated cannulated proximal end of each of the cutting tubes, respectively, for axially urging harvested cores out of the cutting tubes.

9. The apparatus of claim 8, further comprising a transfer tube for receiving a core harvested with the core-cutting tube and pressed out of the core-cutting tube.

10. The apparatus of claim 8, wherein the elongated cannulated proximal end of the cutting tube is open, and the proximal end of the pin extends through the open proximal end of the cutting tube.

11. The apparatus of claim 8, wherein at least one of the sharp cutting edges is formed by a dual bevel.

12. The apparatus of claim 8, wherein the sharp cutting edge on the core-cutting tube is formed by a dual bevel for compacting a harvested bone core.

13. The apparatus of claim 8, further comprising a transfer tube having opposed open ends disposed on the distal end of the core-cutting tube.

14. The apparatus of claim 8, wherein the sharp cutting edge on the core-cutting tube is formed by a dual bevel for compacting a harvested bone core, such that the diameter of the cutting edge on the core-cutting tube is slightly larger than the inner diameter of the core-cutting tube.

15. The apparatus of claim 8, wherein the sharp cutting edge on the socket-cutting tube is formed by a single bevel such that the diameter of the cutting edge is equal to the outer diameter of thicket-cutting tube.

16. The apparatus of claim 8, wherein the slotted window extends along a portion of the tube in which the cylindrical bone core is received.

17. Apparatus for transplanting osteochondral cores in a joint, the apparatus comprising:
- a tube having a longitudinal axis and a smooth distal end for axially receiving a bone core, and an extended cannulated proximal end, the tube including a lumen having an inner diameter, and a slotted window for viewing the bone core received within the lumen;
- a handle coupled to the tube for twisting the cutting tube for removal of the bone core from bone;
- an impacting surface disposed proximally to the tube and configured for receiving axial impacting forces for driving the tube into bone without rotation; and
- a pin having a blunt distal end and a proximal end disposed slidably within the tube, an outer diameter of the distal end of the pin approximating the inner diameter of the lumen, the pin having a collar disposed on the distal end of the pin and being adapted to be slidably advanced within the tube toward the distal end of the tube to press the bone core past the slotted window and out of the distal end of the tube.

18. The apparatus of claim 17, wherein the window has an edge, and at least a portion of the edge is coined in toward the lumen for retaining the bone core within the tube.

19. The apparatus of claim 17, further comprising a transfer tube having opposed open ends for receiving a harvested core pressed out of the tube with the pin.

20. The apparatus of claim 19, wherein the transfer tube is clear to allow viewing of the bone core within the transfer tube.

21. The apparatus of claim 17, wherein the slotted window extends along a portion of the tube in which the cylindrical bone core harvested by the cutting edge is received.

* * * * *